US012110525B2

(12) United States Patent
Sun et al.

(10) Patent No.: US 12,110,525 B2
(45) Date of Patent: Oct. 8, 2024

(54) METHOD FOR ENZYMATIC PREPARATION OF R-3 AMINOBUTYRIC ACID

(71) Applicant: ABIOCHEM BIOTECHNOLOGY CO., LTD., Shanghai (CN)

(72) Inventors: Chuanmin Sun, Shanghai (CN); Zhanbing Cheng, Shanghai (CN); Jianghua Jiao, Shanghai (CN); Shaonan Ding, Shanghai (CN); Zhenhua Tian, Shanghai (CN)

(73) Assignee: ABIOCHEM BIOTECHNOLOGY (GROUP) CO., LTD., Shanghai (CN)

( * ) Notice: Subject to any disclaimer, the term of this patent is extended or adjusted under 35 U.S.C. 154(b) by 130 days.

(21) Appl. No.: 17/539,414

(22) Filed: Dec. 1, 2021

(65) Prior Publication Data

US 2022/0090152 A1 Mar. 24, 2022

Related U.S. Application Data

(62) Division of application No. 16/652,312, filed as application No. PCT/CN2018/092010 on Jun. 20, 2018, now Pat. No. 11,220,701.

(30) Foreign Application Priority Data

Sep. 29, 2017 (CN) .......................... 201710906645.5

(51) Int. Cl.
*C12N 9/88* (2006.01)
*C12P 13/04* (2006.01)

(52) U.S. Cl.
CPC ............... *C12P 13/04* (2013.01); *C12N 9/88* (2013.01); *C12Y 403/01001* (2013.01)

(58) Field of Classification Search
CPC ...... C12N 15/00; C12N 15/70; C12N 9/0008; C12N 9/1096; C12N 9/001; C12N 15/8254; C12N 9/10; C12P 13/001; C12P 13/04; C12P 13/06; C12P 13/005; C12Y 403/01001
USPC ....................................................... 435/128
See application file for complete search history.

(56) References Cited

U.S. PATENT DOCUMENTS 7,256,021 B2  8/2007  Hermann

FOREIGN PATENT DOCUMENTS

JP  2003189863 A  7/2003

OTHER PUBLICATIONS

International Search Report and Written Opinion; PCT Application No. PCT/CN2018/092010; mailed Sep. 10, 2018.
English abstract of JP2003189863; retrieved from www.espacenet.com on Mar. 30, 2020.
Vogel, A. et al. "Converting Asparase into a B-Amino Acid Lyase by Cluster Screening", Chemcatchem, vol. 6; pp. 965-968; Dec. 31, 2014.
Wang, Lijuan et al., "Enhancement of Activity of L-Aspartase from *Escherichia coli*. W. by Directed Evolution." Biochemical and Biophysical Research Communications, vol. 276; pp. 346-349; Dec. 31, 2000.
Zhang, Hongying et al., "Enhancement of the Stability and Activity of Aspartase by Random and Site-Directed Mutagenesis," Biochemical and Biophysical Research Communications, vol. 192, No. 1, pp. 15-21; Apr. 15, 1993.
Leopold, S.R. et al., "Aspartate Ammonia-Lyase [*Escherichia coli*], GenBank: ACI73571.1" GenBank, Jun. 8, 2009.
Davies, et al., "Parallel synthesis of homochiral b-amino acids" The Department of Organic Chemistry, Chemistry Research Laboratory, University of Oxford, Manfield Road, Received May 29, 2007; Accepted Jun. 7, 2007.
Vogel, A. et al. "Converting Asparase into a B-Amino Acid Lyase by Cluster Screening", Chemcatchem 2014, 6, 965-968.
Maenpaa et al., "cylation of b-Amino Esters and Hydrolysis of b-Amino Esters: *Candidda antartica* Lipase A as a Chemoselective Deprotection Catalyst" ChemCatChem 2016, 8, 1226-1232.

*Primary Examiner* — Tekchand Saidha
*Assistant Examiner* — Mohammad Y Meah
(74) *Attorney, Agent, or Firm* — NKL Law; Allen Xue

(57) ABSTRACT

An R-3-aminobutyric acid preparation method with high efficiency and high stereoselectivity. The method comprises using aspartase with stereoisomerization catalytic activity derived from *Escherichia coli* to efficiently convert butenoic acid into R-3-aminobutyric acid. After only 24 h of reaction, the conversion rate is as high as ≥98%, and the ee value is ≥99.9%. The conversion efficiency is greatly improved, the reaction time is shortened, and the production costs are reduced. The method features a high yield, a high conversion rate, low costs, a short production cycle, a simple process, ease of enlargement, suitability for mass production and the like.

7 Claims, No Drawings

Specification includes a Sequence Listing.

SEQUENCE LISTING

<160> NUMBER OF SEQ ID NOS: 6

<210> SEQ ID NO 1
<211> LENGTH: 467
<212> TYPE: PRT
<213> ORGANISM: Artificial Sequence
<220> FEATURE:
<223> OTHER INFORMATION: Aspartase

<400> SEQUENCE: 1

Asn Thr Asp Val Arg Ile Glu Lys Asp Phe Leu Gly Glu Lys Glu Ile
1               5                   10                  15

```
Pro Lys Asp Ala Tyr Tyr Gly Val Gln Thr Ile Arg Ala Thr Glu Asn
            20                  25                  30

Phe Pro Ile Thr Gly Tyr Arg Ile His Pro Glu Leu Ile Lys Ser Leu
            35                  40                  45

Gly Ile Val Lys Lys Ser Ala Ala Leu Ala Asn Met Glu Val Gly Leu
 50                  55                  60

Leu Asp Lys Glu Val Gly Gln Tyr Ile Val Lys Ala Ala Asp Glu Val
 65                  70                  75                  80

Ile Glu Gly Lys Trp Asn Asp Gln Phe Ile Val Asp Pro Ile Gln Gly
                 85                  90                  95

Gly Ala Gly Thr Ser Ile Asn Met Asn Ala Asn Glu Val Ile Ala Asn
            100                 105                 110

Arg Ala Leu Glu Leu Met Gly Glu Gln Lys Gly Asn Tyr Ser Lys Ile
            115                 120                 125

Ser Pro Asn Ser His Val Asn Met Ser Gln Ser Thr Asn Asp Ala Phe
130                 135                 140

Pro Thr Ala Thr His Ile Ala Val Leu Ser Leu Leu Asn Gln Leu Ile
145                 150                 155                 160

Glu Thr Thr Lys Tyr Met Gln Gln Glu Phe Met Lys Lys Ala Asp Glu
                165                 170                 175

Phe Ala Gly Val Ile Lys Met Gly Arg Cys His Leu Gln Asp Ala Val
            180                 185                 190

Pro Ile Leu Leu Gly Gln Glu Phe Glu Ala Tyr Ala Arg Val Ile Ala
            195                 200                 205

Arg Asp Ile Glu Arg Ile Ala Asn Thr Arg Asn Asn Leu Tyr Asp Ile
210                 215                 220

Asn Met Gly Ala Thr Ala Val Gly Thr Gly Leu Asn Ala Asp Pro Glu
225                 230                 235                 240

Tyr Ile Ser Ile Val Thr Glu His Leu Ala Lys Phe Ser Gly His Pro
                245                 250                 255

Leu Arg Ser Ala Gln His Leu Val Asp Ala Thr Gln Asn Thr Asp Cys
            260                 265                 270

Tyr Thr Glu Val Ser Ser Ala Leu Lys Val Cys Met Ile Asn Met Ser
            275                 280                 285

Lys Ile Ala Asn Asp Leu Arg Leu Met Ala Ser Gly Pro Arg Ala Gly
290                 295                 300

Leu Ser Glu Ile Val Leu Pro Ala Arg Gln Pro Gly Ser Ser Ile Ile
305                 310                 315                 320

Pro Gly Met Val Cys Pro Val Met Pro Glu Val Met Asn Gln Val Ala
                325                 330                 335

Phe Gln Val Phe Gly Asn Asp Leu Thr Ile Thr Ser Ala Ser Glu Ala
            340                 345                 350

Gly Gln Phe Glu Leu Asn Val Met Glu Pro Val Leu Phe Phe Asn Leu
            355                 360                 365

Ile Gln Ser Ile Ser Ile Met Thr Asn Val Phe Lys Ser Phe Thr Glu
370                 375                 380

Asn Cys Leu Lys Gly Ile Lys Ala Asn Glu Glu Arg Met Lys Glu Tyr
385                 390                 395                 400

Val Glu Lys Ser Ile Gly Ile Ile Thr Ala Ile Asn Pro His Val Gly
                405                 410                 415

Tyr Glu Thr Ala Ala Lys Leu Ala Arg Glu Ala Tyr Leu Thr Gly Glu
            420                 425                 430
```

Ser Ile Arg Glu Leu Cys Ile Lys Tyr Gly Val Leu Thr Glu Glu Gln
        435                 440                 445

Leu Asn Glu Ile Leu Asn Pro Tyr Glu Met Ile His Pro Gly Ile Ala
    450                 455                 460

Gly Arg Lys
465

<210> SEQ ID NO 2
<211> LENGTH: 1401
<212> TYPE: DNA
<213> ORGANISM: Artificial Sequence
<220> FEATURE:
<223> OTHER INFORMATION: Aspartase

<400> SEQUENCE: 2

| | | | | |
|---|---|---|---|---|
| aacaccgatg | tgcgcattga | aaggacttc | ctgggtgaaa | aggaaatccc gaaggatgcc | 60 |
| tattacggcg | tgcagaccat | ccgtgccaca | gagaactttc | ctatcaccgg ctaccgcatc | 120 |
| catccggaac | tgattaagag | cctgggcatt | gtgaagaaaa | cgccgcact ggcaaacatg | 180 |
| gaggtgggtc | tgctggataa | ggaagtgggt | cagtacatcg | tgaaggccgc cgacgaagtt | 240 |
| attgaaggta | gtggaacga | tcagtttatc | gtggacccga | ttcagggcgg cgcaggtaca | 300 |
| agcattaata | tgaacgccaa | cgaagtgatc | gcaaaccgcg | ccctggaact gatgggtgag | 360 |
| gaaaagggca | actatagcaa | gatcagcccg | aacagccacg | ttaacatgag ccagagcacc | 420 |
| aatgatgcat | ttccgaccgc | aacccatatt | gccgtgctga | gtctgctgaa tcagctgatc | 480 |
| gagaccacca | gtacatgca | gcaggagttt | atgaagaagg | ccgacgaatt cgccggcgtt | 540 |
| attaaaatgg | ccgctgcca | tctgcaagac | gccgttccga | ttctgctggg tcaggagttt | 600 |
| gaggcttatg | ctcgtgtgat | cgcacgtgac | attgagcgca | tcgccaatac ccgtaacaac | 660 |
| ctgtatgata | tcaacatggg | cgcaaccgcc | gttggcacag | gctgaatgc agacccggag | 720 |
| tacattagca | tcgttaccga | gcacctggcc | aaatttagcg | tcatccgct gcgtagtgcc | 780 |
| cagcatctgg | ttgatgccac | ccagaataca | gattgctaca | ccgaggtgag cagtgccctg | 840 |
| aaagtgtgca | tgatcaatat | gagtaagatt | gccaacgacc | tgcgcttaat ggcaagtggc | 900 |
| ccgcgcgcag | gcctgagcga | aattgttctg | cctgcacgcc | aaccgggcag cagcatcatc | 960 |
| cctggtatgg | tgtgtccggt | gatgccggaa | gtgatgaacc | aggttgcctt ccaggtgttc | 1020 |
| ggtaacgacc | tgaccatcac | aagcgcaagc | gaagcaggcc | agttcgagtt aaacgtgatg | 1080 |
| gaacctgtgc | tgttttttaa | cttaattcag | agcatcagta | ttatgacaaa tgtttttaag | 1140 |
| tcttttaccg | aaaactgtct | gaaaggtatc | aaggccaacg | aggaacgcat gaaagagtat | 1200 |
| gtggaaaaaa | gcattggcat | catcaccgcc | atcaacccgc | atgtgggcta tgagacagcc | 1260 |
| gccaaactgg | cccgcgaagc | ctatttaacc | ggcgagagta | ttcgcgagct gtgtatcaag | 1320 |
| tacggcgtgc | tgaccgaaga | gcagctgaac | gagatcctga | atccgtacga tgatgatccat | 1380 |
| cctggcattg | caggtcgcaa | a | | | 1401 |

<210> SEQ ID NO 3
<211> LENGTH: 492
<212> TYPE: PRT
<213> ORGANISM: Artificial Sequence
<220> FEATURE:
<223> OTHER INFORMATION: Aspartase

<400> SEQUENCE: 3

Cys Leu Lys Gln Ile Ile Gly Ser Leu Lys Lys Lys Val His Met Ser
1               5                   10                  15

```
Asn Asn Ile Arg Ile Glu Glu Asp Leu Leu Gly Thr Arg Glu Val Pro
        20                  25                  30

Ala Asp Ala Tyr Tyr Gly Val His Thr Leu Arg Ala Ile Glu Asn Phe
        35                  40                  45

Tyr Ile Ser Asn Asn Lys Ile Ser Asp Ile Pro Glu Phe Val Arg Gly
        50                  55                  60

Met Val Met Val Lys Lys Ala Ala Met Ala Asn Lys Glu Leu Gln
65                  70                  75                  80

Thr Ile Pro Lys Ser Val Ala Asn Ala Ile Ile Ala Ala Cys Asp Glu
                85                  90                  95

Val Leu Asn Asn Gly Lys Cys Met Asp Gln Phe Pro Val Asp Val Tyr
            100                 105                 110

Gln Gly Gly Ala Gly Thr Ser Val Asn Met Asn Thr Asn Glu Val Leu
                115                 120                 125

Ala Asn Ile Gly Leu Glu Leu Met Gly His Gln Lys Gly Glu Tyr Gln
130                 135                 140

Tyr Leu Asn Pro Asn Asp His Val Asn Lys Cys Gln Ser Thr Asn Asp
145                 150                 155                 160

Ala Tyr Pro Thr Gly Phe Arg Ile Ala Val Tyr Ser Ser Leu Ile Lys
                165                 170                 175

Leu Val Asp Ala Ile Asn Gln Leu Arg Glu Gly Phe Glu Arg Lys Ala
            180                 185                 190

Val Glu Phe Gln Asp Ile Leu Lys Met Gly Arg Cys Gln Leu Gln Asp
            195                 200                 205

Ala Val Pro Met Thr Leu Gly Gln Glu Phe Arg Ala Phe Ser Ile Leu
            210                 215                 220

Leu Lys Glu Glu Val Lys Asn Ile Gln Arg Thr Ala Glu Leu Leu Leu
225                 230                 235                 240

Glu Val Asn Leu Gly Ala Thr Ala Ile Gly Thr Gly Leu Asn Thr Pro
                245                 250                 255

Lys Glu Tyr Ser Pro Leu Ala Val Lys Lys Leu Ala Glu Val Thr Gly
                260                 265                 270

Phe Pro Cys Val Pro Ala Glu Asp Leu Ile Glu Ala Thr Ser Asp Cys
            275                 280                 285

Gly Ala Tyr Val Met Val His Gly Ala Leu Lys Arg Leu Ala Val Lys
            290                 295                 300

Met Ser Lys Ile Cys Asn Asp Leu Arg Leu Leu Ser Ser Gly Pro Arg
305                 310                 315                 320

Ala Gly Leu Asn Glu Ile Asn Leu Pro Glu Leu Gln Ala Gly Ser Ser
                325                 330                 335

Ile Ile Pro Ala Met Val Cys Pro Val Val Pro Glu Val Val Asn Gln
            340                 345                 350

Val Cys Phe Lys Val Ile Gly Asn Asp Thr Thr Val Thr Met Ala Ala
            355                 360                 365

Glu Ala Gly Gln Leu Gln Leu Asn Val Met Glu Pro Val Ile Gly Gln
            370                 375                 380

Ala Met Phe Glu Ser Val His Ile Leu Thr Asn Ala Cys Tyr Asn Leu
385                 390                 395                 400

Leu Glu Lys Cys Ile Asn Gly Ile Thr Ala Asn Lys Glu Val Cys Glu
                405                 410                 415

Gly Tyr Val Tyr Asn Ser Ile Gly Ile Val Thr Tyr Leu Asn Pro Phe
            420                 425                 430
```

```
Ile Gly His His Asn Gly Asp Ile Val Gly Lys Ile Cys Ala Glu Thr
            435                 440                 445

Gly Lys Ser Val Arg Glu Val Val Leu Glu Arg Gly Leu Leu Thr Glu
        450                 455                 460

Ala Glu Leu Asp Asp Ile Phe Ser Val Gln Asn Leu Met His Pro Ala
465                 470                 475                 480

Tyr Lys Ala Lys Arg Tyr Thr Asp Glu Ser Glu Gln
                485                 490
```

<210> SEQ ID NO 4
<211> LENGTH: 1476
<212> TYPE: DNA
<213> ORGANISM: Artificial Sequence
<220> FEATURE:
<223> OTHER INFORMATION: Aspartase

<400> SEQUENCE: 4

```
tgcctgaaac aaatcattgg tagcctgaag aaaaaagtgc acatgagcaa taacattcgc        60
atcgaagagg atctgctggg tacacgtgaa gtgccggcag atgcctacta cggtgtgcat       120
acactgcgcg ccatcgaaaa tttttacatc agcaataata aaatcagcga tatcccggaa       180
ttcgtgcgcg catggttat ggtgaaaaaa gccgccgcaa tggccaacaa ggaactgcag         240
accattccga gagtgtggc aaacgccatt atcgccgcct gtgatgaagt gctgaacaat         300
ggtaaatgca tggatcagtt tccggtggac gtgtatcaag gcggcgccgg taccagcgtg        360
aacatgaaca ccaatgaggt gctggccaac attggtctgg agctgatggg tcaccagaaa       420
ggcgaatacc agtacctgaa cccgaacgat acgtgaaca gtgtcagag cacaaatgac         480
gcatacccga caggcttcg tattgccgtg tacagtagcc tgatcaagct ggtggatgcc        540
atcaatcagc tgcgtgaagg cttcgagcgt aaggccgttg aatttcagga catcctgaaa       600
atgggtcgtt gtcagctgca ggatgcagtg ccgatgaccc tgggtcagga atttcgcgca       660
ttcagcatcc tgttaaaaga ggaagtgaaa aacatccagc gtaccgccga actgctgctg       720
gaagttaacc tgggtgccac cgccatcggc acaggcctga ataccccgaa agagtatagc       780
ccgctggccg ttaaaaaact ggcagaggtg accggtttcc cgtgtgtgcc ggcagaggat       840
ctgatcgaag caaccagcga ttgcggtgct tatgttatgg tgcatggtgc cctgaaacgc       900
ctggccgtta agatgagtaa atctgtaat gacctgcgtc tgctgagcag cggtcctcgt        960
gcaggcctga acgagatcaa cctgccggaa ctgcaggccg cagtagcat catcccggcc      1020
atggtttgcc ctgtggtgcc ggaggtggtg aatcaggtgt gcttcaaggt gatcggcaat      1080
gacaccaccg tgacaatggc cgcagaggca ggccagctgc aactgaacgt gatggagccg      1140
gtgattggcc aggccatgtt tgaaagcgtg cacatcttaa ccaacgcctg ctacaacctg      1200
ctggagaaat gcatcaatgg tattaccgcc aacaaagaag tttgcgaggg ttacgtgtac      1260
aacagcattg gcatcgtgac ctatctgaat ccgtttattg gccatcacaa cggcgacatt      1320
gtgggcaaga tttgcgcaga gaccggcaaa agtgttcgcg aagtggttct ggagcgcggt      1380
ttactgaccg aggccgaact ggatgacatt ttcagcgttc aaaatctgat gcacccggcc      1440
tacaaagcca aacgctacac agacgaaagc gagcaa                                1476
```

<210> SEQ ID NO 5
<211> LENGTH: 492
<212> TYPE: PRT
<213> ORGANISM: Escherichia coli

<400> SEQUENCE: 5

```
Cys Leu Lys Gln Ile Ile Gly Ser Leu Lys Lys Val His Met Ser
1               5                  10                 15

Asn Asn Ile Arg Ile Glu Glu Asp Leu Leu Gly Thr Arg Glu Val Pro
            20                  25                 30

Ala Asp Ala Tyr Tyr Gly Val His Thr Leu Arg Ala Ile Glu Asn Phe
        35                  40                  45

Tyr Ile Ser Asn Asn Lys Ile Ser Asp Ile Pro Glu Phe Val Arg Gly
    50                  55                  60

Met Val Met Val Lys Lys Ala Ala Met Ala Asn Lys Glu Leu Gln
65              70                  75                  80

Thr Ile Pro Lys Ser Val Ala Asn Ala Ile Ala Ala Cys Asp Glu
                85                  90                  95

Val Leu Asn Asn Gly Lys Cys Met Asp Gln Phe Pro Val Asp Val Tyr
                100                 105                110

Gln Gly Gly Ala Gly Thr Ser Val Asn Met Asn Thr Asn Glu Val Leu
            115                 120                 125

Ala Asn Ile Gly Leu Glu Leu Met Gly His Gln Lys Gly Glu Tyr Gln
130                 135                 140

Tyr Leu Asn Pro Asn Asp His Val Asn Lys Cys Gln Ser Thr Asn Asp
145                 150                 155                 160

Ala Tyr Pro Thr Gly Phe Arg Ile Ala Val Tyr Ser Ser Leu Ile Lys
                165                 170                 175

Leu Val Asp Ala Ile Asn Gln Leu Arg Glu Gly Phe Glu Arg Lys Ala
            180                 185                 190

Val Glu Phe Gln Asp Ile Leu Lys Met Gly Arg Thr Gln Leu Gln Asp
            195                 200                 205

Ala Val Pro Met Thr Leu Gly Gln Glu Phe Arg Ala Phe Ser Ile Leu
            210                 215                 220

Leu Lys Glu Glu Val Lys Asn Ile Gln Arg Thr Ala Glu Leu Leu Leu
225                 230                 235                 240

Glu Val Asn Leu Gly Ala Thr Ala Ile Gly Thr Gly Leu Asn Thr Pro
                245                 250                 255

Lys Glu Tyr Ser Pro Leu Ala Val Lys Lys Leu Ala Glu Val Thr Gly
                260                 265                 270

Phe Pro Cys Val Pro Ala Glu Asp Leu Ile Glu Ala Thr Ser Asp Cys
            275                 280                 285

Gly Ala Tyr Val Met Val His Gly Ala Leu Lys Arg Leu Ala Val Lys
            290                 295                 300

Met Ser Lys Ile Cys Asn Asp Leu Arg Leu Leu Ser Ser Gly Pro Arg
305                 310                 315                 320

Ala Gly Leu Asn Glu Ile Asn Leu Pro Glu Leu Gln Ala Gly Ser Ser
                325                 330                 335

Ile Met Pro Ala Lys Val Asn Pro Val Val Pro Glu Val Val Asn Gln
            340                 345                 350

Val Cys Phe Lys Val Ile Gly Asn Asp Thr Thr Val Thr Met Ala Ala
            355                 360                 365

Glu Ala Gly Gln Leu Gln Leu Asn Val Met Glu Pro Val Ile Gly Gln
370                 375                 380

Ala Met Phe Glu Ser Val His Ile Leu Thr Asn Ala Cys Tyr Asn Leu
385                 390                 395                 400

Leu Glu Lys Cys Ile Asn Gly Ile Thr Ala Asn Lys Glu Val Cys Glu
                405                 410                 415
```

```
Gly Tyr Val Tyr Asn Ser Ile Gly Ile Val Thr Tyr Leu Asn Pro Phe
            420                 425                 430

Ile Gly His His Asn Gly Asp Ile Val Gly Lys Ile Cys Ala Glu Thr
        435                 440                 445

Gly Lys Ser Val Arg Glu Val Val Leu Glu Arg Gly Leu Leu Thr Glu
    450                 455                 460

Ala Glu Leu Asp Asp Ile Phe Ser Val Gln Asn Leu Met His Pro Ala
465                 470                 475                 480

Tyr Lys Ala Lys Arg Tyr Thr Asp Glu Ser Glu Gln
                485                 490

<210> SEQ ID NO 6
<211> LENGTH: 1476
<212> TYPE: DNA
<213> ORGANISM: Escherichia coli

<400> SEQUENCE: 6
```

| | | | | | |
|---|---|---|---|---|---|
| tgcctgaaac | agatcatcgg | ttctctgaaa | aaaaaagttc | acatgtctaa | caacatccgt | 60 |
| atcgaagaag | acctgctggg | tacccgtgaa | gttccggctg | acgcttacta | cggtgttcac | 120 |
| accctgcgtg | ctatcgaaaa | cttctacatc | tctaacaaca | aaatctctga | catcccggaa | 180 |
| ttcgttcgtg | gtatggttat | ggttaaaaaa | gctgctgcta | tggctaacaa | agaactgcag | 240 |
| accatcccga | atctgttgc | taacgctatc | atcgctgctt | gcgacgaagt | tctgaacaac | 300 |
| ggtaaatgca | tggaccagtt | cccggttgac | gtttaccagg | gtggtgctgg | tacctctgtt | 360 |
| aacatgaaca | ccaacgaagt | tctggctaac | atcggtctgg | aactgatggg | tcaccagaaa | 420 |
| ggtgaatacc | agtacctgaa | cccgaacgac | cacgttaaca | atgccagtc | taccaacgac | 480 |
| gcttacccga | ccggtttccg | tatcgctgtt | tactcttctc | tgatcaaact | ggttgacgct | 540 |
| atcaaccagc | tgcgtgaagg | tttcgaacgt | aaagctgttg | aattccagga | catcctgaaa | 600 |
| atgggtcgta | cccagctgca | ggacgctgtt | ccgatgaccc | tgggtcagga | attccgtgct | 660 |
| ttctctatcc | tgctgaaaga | agaagttaaa | aacatccagc | gtaccgctga | actgctgctg | 720 |
| gaagttaacc | tgggtgctac | cgctatcggt | accggtctga | cacccccgaa | agaatactct | 780 |
| ccgctggctg | ttaaaaaact | ggctgaagtt | accggtttcc | cgtgcgttcc | ggctgaagac | 840 |
| ctgatcgaag | ctacctctga | ctgcggtgct | tacgttatgg | ttcacggtgc | tctgaaacgt | 900 |
| ctggctgtta | aaatgtctaa | aatctgcaac | gacctgcgtc | tgctgtcttc | tggtccgcgt | 960 |
| gctggtctga | cgaaatcaa | cctgccggaa | ctgcaggctg | ttcttctat | catgccggct | 1020 |
| aaagttaacc | cggttgttcc | ggaagttgtt | aaccaggttt | gcttcaaagt | tatcggtaac | 1080 |
| gacaccaccg | ttaccatggc | tgctgaagct | ggtcagctgc | agctgaacgt | tatggaaccg | 1140 |
| gttatcggtc | aggctatgtt | cgaatctgtt | cacatcctga | ccaacgcttg | ctacaacctg | 1200 |
| ctggaaaaat | gcatcaacgg | tatcaccgct | aacaaagaag | tttgcgaagg | ttacgttac | 1260 |
| aactctatcg | gtatcgttac | ctacctgaac | ccgttcatcg | gtcaccacaa | cggtgacatc | 1320 |
| gttggtaaaa | tctgcgctga | aaccggtaaa | tctgttcgtg | aagttgttct | ggaacgtggt | 1380 |
| ctgctgaccg | aagctgaact | ggacgacatc | ttctctgttc | agaacctgat | gcacccggct | 1440 |
| tacaaagcta | aacgttacac | cgacgaatct | gaacag | | | 1476 |

METHOD FOR ENZYMATIC PREPARATION OF R-3 AMINOBUTYRIC ACID

TECHNICAL FIELD

The invention belongs to the field of biotechnology, and specifically relates to a method for enzymatic preparation of R-3-aminobutyric acid.

BACKGROUND

Dolutegravir is a new anti-HIV drug from GlaxoSmithKline, which was approved by the FDA in 2013 and acknowledges its breakthrough. R-3-aminobutyric acid is an important intermediate for the production of Dolutegravir. At present, the existing preparation methods mainly include chemical synthesis method and enzymatic method.

Chemical synthesis method, such as Tetrahedron: Asymmetry 18 (2007) 1554-1566 reported that formaldehyde is used as a raw material, and tert-Butyl-2-butenoate is obtained by the Horner-Wadsworth-Emmons reaction, and then R-tert-Butyl-3-aminobutanoate was obtained by addition reaction, catalysis and hydrogenation. R-3-aminobutyric acid is finally obtained by hydrolysis. However, this reaction requires a low temperature of −78° C. The reaction conditions are harsh and the operation is difficult.

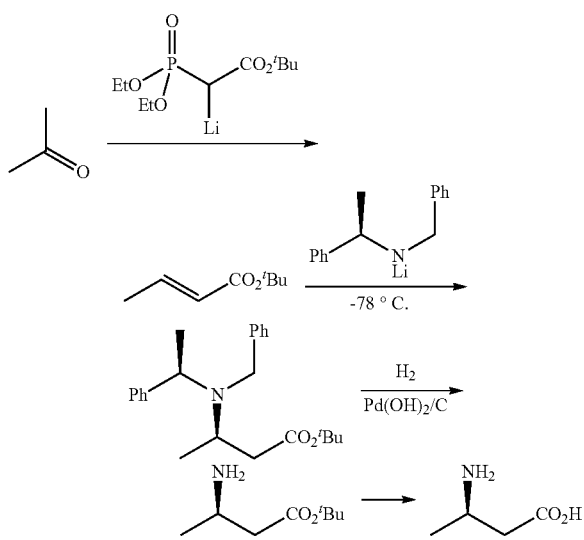

For another example, CN104370755 discloses a method wherein ethyl acetoacetate is used as a raw material, which is condensed with acetamide, and then R-3-aminobutyric acid is obtained by asymmetric hydrogenation and hydrolysis. However, this method requires an expensive asymmetric hydrogenation catalyst. The method has high production cost and heavy metal pollution, and is not suitable for industrial production.

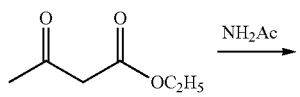

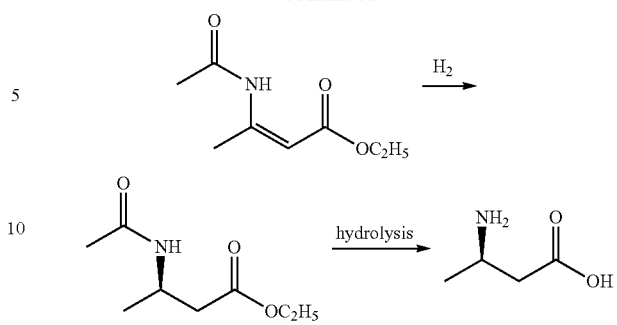

Enzymatic method, such as ChemCatChem 2016, 8, 1226-1232 reported that racemic tert-Butyl-3-aminobutanoate is used as raw material, R-type tert-butyl 3-butyramidobutyrate is obtained by stereoselectivity catalysis with lipase A (CLA-A) derived from *Candida antarctica*, and R-3-aminobutyric acid is obtained by catalytic hydrolysis with CAL-A. However, the conversion rate of this method is low, and unreacted raw materials are wasted.

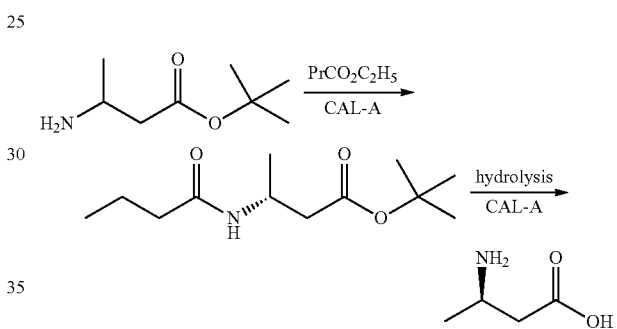

In addition, ChemCatChem, 2014, 6, 965-968 reported a method for producing R-3-aminobutyric acid by catalyzing butenoic acid with an aspartase mutant BSASP-C6 derived from *Bacillus* YM55-1. However, the conversion rate in this method of 100 hours of reaction is only 60%. The reaction time is long, and the conversion rate is low; and as the reaction time increases, the ee value of the product decreases.

Therefore, there is an urgent need in the art to develop an environmentally friendly, efficient, and highly stereoselective method for preparing R-3-aminobutyric acid.

SUMMARY OF THE INVENTION

The purpose of the present invention is to provide an R-3-aminobutyric acid preparation method with high efficiency and high stereoselectivity. The method can significantly improve the ee value and conversion rate of R-3-aminobutyric acid and shorten the reaction time.

In a first aspect of the invention, it provides a method for producing an R-3-aminobutyric acid, which comprises the steps of:

(1) using butenoic acid as a substrate and carrying out a stereoisomeric catalytic reaction shown in equation I to form the R-3-aminobutyric acid under the catalysis of aspartase in a reaction system;

Equation I

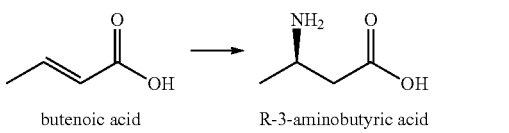

(b) optionally, isolating the R-3-aminobutyric acid from the reaction system after the reaction of the step (1); wherein, the aspartase is derived from *E. coli*.

In another preferred embodiment, the aspartase is a wild type or mutant.

In another preferred embodiment, the ee value of the R-3-aminobutyric acid is ≥99.5%, preferably ≥99.7%, more preferably ≥99.8%, and most preferably 99.9%.

In another preferred embodiment, the conversion rate of the reaction is ≥90%, preferably ≥95%, more preferably ≥98%, still more preferably ≥99%, most preferably 100%.

In another preferred embodiment, the mutant has an amino acid mutation in the amino acid sequence corresponding to the wild type aspartase, wherein the amino acid mutation is selected from the group consisting of threonine (T) at position 204, methionine (M) at position 338, Lysine (K) at position 341, asparagine (N) at position 343, or a combination thereof.

In another preferred embodiment, the mutation of the mutant is selected from the group consisting of T204C, M338I, K341M, N343C, or a combination thereof. In another preferred embodiment, the amino acid sequence of the wild type aspartase is shown in SEQ ID NO: 5.

In another preferred embodiment, the aspartase is selected from the group consisting of:
(a) a polypeptide having an amino acid sequence as shown in SEQ ID NO: 5;
(b) a polypeptide having an amino acid sequence as shown in SEQ ID NO: 3; or
(c) a polypeptide derived from the polypeptide having an amino acid sequence shown in SEQ ID NO: 5 or SEQ ID NO: 3 and formed by substitution, deletion, or addition of one or more, preferably 1-20, more preferably 1-15, more preferably 1-10, more preferably 1-8, more preferably 1-3, and most preferably one amino acid residue(s) of the amino acid sequence shown in SEQ ID NO: 5 or SEQ ID NO: 3, and having a function of the polypeptide of (a) or (b).

In another preferred embodiment, the amino acid sequence of the aspartase has at least 70%, preferably at least 75%, 80%, 85%, 90%, and more preferably at least 95%, 96%, 97%, 98%, or 99% sequence identity of the amino acid sequence shown in SEQ ID NO: 5 or SEQ ID NO: 3.

In another preferred embodiment, the aspartase is in a form selected from the group consisting of resting cells, bacterial cells, crude enzyme solution, pure enzyme, crude enzyme powder, immobilized enzyme, free enzyme, fermentation solution, or a combination thereof.

In another preferred embodiment, the concentration of the aspartase in the reaction system is 0.5-5 U/ml.

In another preferred embodiment, the concentration of the butenoic acid in the reaction system is 100 mM-1000 mM.

In another preferred embodiment, an ammonium source is also present in the reaction system.

In another preferred embodiment, the ammonium source is selected from the group consisting of ammonium hydroxide, $NH_4^+$ salt (such as $NH_4Cl$), or a combination thereof In another preferred embodiment, the molar ratio of the ammonium source to the butenoic acid is 1:1 to 1:3.

In another preferred embodiment, the pH of the reaction system in step (a) is 7.0-9.5, preferably 7.5-9.0, more preferably 8.0-8.5.

In another preferred embodiment, the reaction temperature in step (a) is 20-60° C., preferably 30-50° C., more preferably 35-45° C.

In another preferred embodiment, the reaction time in step (a) is 0.5 h-72 h, preferably 2 h-48 h, and more preferably 4 h-24 h.

In a second aspect of the invention, it provides a use of aspartase for preparing a preparation for catalyzing the stereoisomeric catalytic reaction as below:

Equation I

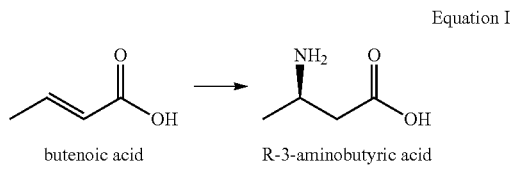

wherein, the aspartase is derived from *E. coli*.

In another preferred embodiment, the aspartase is a wild type or mutant.

In another preferred embodiment, the aspartase is as defined in the first aspect of the present invention.

In a third aspect of the invention, it provides an R-3-aminobutyric acid production strain expressing a polypeptide, and the polypeptide is an exogenous aspartase derived from *E. coli* and is used to catalyze the stereoisomeric catalytic reaction as below:

Equation I

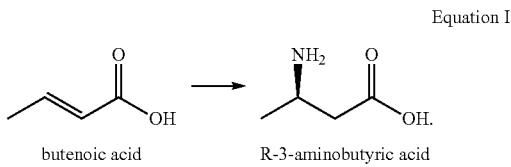

In another preferred embodiment, the aspartase is a wild type or mutant.

In another preferred embodiment, the mutant has an amino acid mutation in the amino acid sequence corresponding to the wild type aspartase, wherein the amino acid mutation is selected from the group consisting of threonine (T) at position 204, methionine (M) at position 338, Lysine (K) at position 341, asparagine (N) at position 343, or a combination thereof.

In another preferred embodiment, the mutation is selected from the group consisting of T204C, M338I, K341M, N343C, or a combination thereof.

In another preferred embodiment, the production strain is a bacteria. Preferably, the production strain is *E. coli*. More preferably, the production strain is *E. coli* BL21 (DE3).

In a forth aspect of the invention, it provides a method for producing an R-3-aminobutyric acid, which comprises the steps of:
1) culturing the production strain of the third aspect of the invention under production conditions to obtain the R-3-aminobutyric acid;
2) optionally, isolating the R-3-aminobutyric acid from the culture system of 1).

In a fifth aspect of the invention, it provides an aspartase having stereoisomeric catalytic activity, wherein the amino acid sequence of the aspartase is shown in SEQ ID NO: 3.

In another preferred embodiment, the aspartase is in a form selected from the group consisting of bacterial cells, crude enzyme solution, pure enzyme, crude enzyme powder, immobilized enzyme, free enzyme, fermentation solution, or a combination thereof.

In a six aspect of the invention, it provides a polynucleotide encoding the aspartase of the fifth aspect of the invention.

In another preferred embodiment, the polynucleotide is selected from the group consisting of:
  (a) a polynucleotide encoding a polypeptide as shown in SEQ ID NO: 3.
  (b) a polynucleotide having a sequence as shown in SEQ ID NO: 4;
  (c) a polynucleotide having a nucleotide sequence of ≥95% (preferably ≥98%, more preferably ≥99%) homologous to the sequence of SEQ ID NO: 4, and encoding a polypeptide as shown in SEQ ID NO: 3;
  (d) a polynucleotide complementary to the polynucleotide of any of (a) to (c).

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

MODES FOR CARRYING OUT THE PRESENT INVENTION

After extensive and intensive studies and screening, the inventors have unexpectedly found an R-3-aminobutyric acid preparation method with high efficiency and high stereoselectivity. This method utilizes an aspartase derived from E. coli that has stereoisomeric catalytic activity to efficiently and highly stereoselectively convert butenoic acid to R-3-aminobutyric acid. In particular, the mutant aspartase of the invention has very excellent high stereoselectivity and high conversion rate, thereby greatly improving the conversion efficiency, shortening the reaction time, and reducing the production cost. Experiments show that after only 24 h of reaction, the conversion rate is as high as ≥98% and the ee value is ≥99.9%. The method features a high yield, a high conversion rate, low costs, a short production cycle, a simple process, ease of enlargement, suitability for mass production and the like. The present invention has been completed on the basis of this.

Terms
ee Value

As used herein, "ee value" or "enantiomeric excess" is used to characterize the excess value of one enantiomer relative to another enantiomer in a chiral molecule, which is usually expressed as a percentage.

Aspartase

As used herein, the terms "enzyme", "polypeptide", "aspartase", "polypeptide of the invention", "aspartase of the invention" or "AspA" have the same meaning and can be used interchangeably herein. The terms all refer to proteins derived from E. coli that have stereoisomeric catalytic activity to produce R-3-aminobutyric acid with butenoic acid. Preferably, the polypeptide of the present invention refers to the enzyme as defined in the first aspect of the invention.

Aspartase is a kind of deaminase. It is a lyase that reversibly catalyzes the deamination of L-aspartic acid to fumaric acid. EC 4.3.1.1 is widely present in bacteria, yeast. Higher plants (such as shoots or leaves of beans and so on) also contain low concentrations of aspartase. Higher animals do not have this enzyme.

In the present invention, the aspartase derived from E. coli is defined as AspA.

In the present invention, the aspartase in Bacillus is defined as AspB, and the mutant is BSASP-C6.

Based on the knowledge of the prior art, it is not difficult for the ordinary skilled in the art to know that the change of a few amino acid residues in certain regions of the polypeptide, such as non-important regions, will not substantially change biological activity. For example, the sequence obtained by appropriate substitution of certain amino acids will not affect the activity (see Watson et al., Molecular Biology of The Gene, Fourth Edition, 1987, The Benjamin/Cummings Pub. Co. P224). Thus, an ordinary skilled in the art would be able to perform such a substitution and ensure that the obtained molecule still has the desired biological activity.

In a specific embodiment, the aspartase of the invention is a wild-type or mutant.

In a preferred embodiment, the mutant has an amino acid mutation in the amino acid sequence corresponding to the wild type aspartase, wherein the amino acid mutation is selected from the group consisting of threonine (T) at position 204, methionine (M) at position 338, Lysine (K) at position 341, asparagine (N) at position 343, or a combination thereof.

In another preferred embodiment, the mutation is selected from the group consisting of T204C, M338I, K341M, N343C, or a combination thereof.

In another preferred embodiment, the amino acid sequence of the wild type aspartase is shown in SEQ ID NO: 5.

In another preferred example, the aspartase is selected from the group consisting of:
  (a) a polypeptide having an amino acid sequence as shown in SEQ ID NO: 5;
  (b) a polypeptide having an amino acid sequence as shown in SEQ ID NO: 3; or
  (c) a polypeptide derived from the polypeptide having an amino acid sequence shown in SEQ ID NO: 5 or SEQ ID NO: 3 and formed by substitution, deletion, or addition of one or more, preferably 1-20, more preferably 1-15, more preferably 1-10, more preferably 1-8, more preferably 1-3, and most preferably one amino acid residue(s) of the amino acid sequence shown in SEQ ID NO: 5 or SEQ ID NO: 3, and having a function of the polypeptide of (a) or (b).

In another preferred embodiment, the amino acid sequence of the aspartase has at least 70%, preferably at least 75%, 80%, 85%, 90%, and more preferably at least 95%, 96%, 97%, 98%, or 99% sequence identity of the amino acid sequence shown in SEQ ID NO: 5 or SEQ ID NO: 3.

In another preferred example, the aspartase is in a form selected from the group consisting of bacterial cells, crude enzyme solution, pure enzyme, crude enzyme powder, immobilized enzyme, free enzyme, fermentation solution, or a combination thereof.

In a specific embodiment, the amino acid sequence of the aspartase is shown in SEQ ID NO: 3, and the nucleic acid sequence encoding the polypeptide is shown in SEQ ID NO: 4.

In a specific embodiment, the amino acid sequence of the aspartase is shown in SEQ ID NO: 5, and the nucleic acid sequence encoding the polypeptide is shown in SEQ ID NO: 6.

In the present invention, the aspartase includes a mutant in which at most 20, preferably at most 10, another preferably at most 8, still preferably at most 3, more preferably at most 2, and most preferably at most 1 amino acid(s) is substituted by an amino acid of similar or close property in comparison with the polypeptide having an amino acid sequence as shown in SEQ ID NO: 5 or SEQ ID NO: 3. These mutants with conservative variant are formed by amino acid substitutions as shown in the table below.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides the polynucleotide encoding the polypeptide of the present invention. The term "polynucleotide encoding a polypeptide" may include a polynucleotide that encodes the polypeptide, or a polynucleotide that also includes additional coding and/or non-coding sequences.

Therefore, as used herein, "comprising", "having" or "including" includes "containing", "consisting mainly of", "consisting essentially of", and "consisting of". "Consisting mainly of", "consisting essentially of" and "consisting of" are subordinate concepts of "comprising", "having" or "including".

In a specific embodiment, the homology or sequence identity may be 80% or more, preferably 90% or more, more preferably 95%-98%, and most preferably 99% or more.

Method for determining sequence homology or identity that are well known to the ordinary skilled in the art includes, but are not limited to: Computer Molecular Biology, edited by Lesk, A. M., Oxford University Press, New York, 1988; Biocomputing; Biocomputing: Informatics and Genome Projects, edited by Smith, D. W., Academic Press, New York, 1993; Computer Analysis of Sequence Data, Part I, edited by Griffin, A. M. and Griffin, H. G., Humana Press, New Jersey, 1994; Sequence Analysis in Molecular Biology, von Heinje, G., Academic Press, 1987, and Sequence Analysis Primer, edited by Gribskov, M. and Devereux, J., M Stockton Press, New York, 1991 and Carillo, H. & Lipman, D., SIAM J. Applied Math., 48:1073(1988). The preferred method for determining identity is to obtain the greatest match between the sequences tested. Methods for determining identity are compiled into publicly available computer programs. Preferred computer program method for determining identity between two sequences includes, but are not limited to, the GCG software package (Devereux, J. et al., 1984), BLASTP, BLASTN, and FASTA (Altschul, S, F. et al., 1990). The BLASTX program is available to the public from NCBI and other sources (BLAST Handbook, Altschul, S. et al., NCBI NLM NIH Bethesda, Md. 20894; Altschul, S. et al., 1990). The well-known Smith Waterman algorithm can also be used to determine identity.

Method for Producing R-3-Aminobutyric Acid

The invention provides a method for preparing R-3-aminobutyric acid with high efficiency and high stereoselectivity. The method of the invention is as described in the first aspect of the invention. The method utilizes an aspartase derived from E. coli that has stereoisomeric catalytic activity to efficiently and highly stereoselectively convert butenoic acid to R-3-aminobutyric acid. The method greatly improves conversion efficiency, shortens reaction time, and reduces production costs.

In a preferred embodiment, the method for producing R-3-aminobutyric acid comprises the steps of:
(1) using butenoic acid as a substrate and carrying out a stereoisomeric catalytic reaction shown in equation I to form the R-3-aminobutyric acid under the catalysis of aspartase in a reaction system;

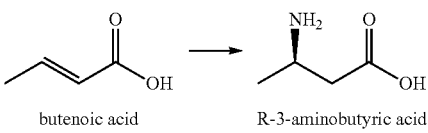

Equation I butenoic acid     R-3-aminobutyric acid (b) optionally, isolating the R-3-aminobutyric acid from the reaction system after the reaction of the step (1); wherein, the aspartase is derived from E. coli.

In another preferred example, the ee value of the R-3-aminobutyric acid is ≥99.5%, preferably ≥99.7%, more preferably ≥99.8%, and most preferably 99.9%.

In another preferred example, the conversion rate of the reaction is ≥90%, preferably ≥95%, more preferably ≥98%, still more preferably ≥99%, most preferably 100%.

In another preferred embodiment, the method for producing R-3-aminobutyric acid comprises:
1) culturing the R-3-aminobutyric acid production strain of the present invention under production conditions to obtain R-3-aminobutyric acid;
2) optionally, isolating the R-3-aminobutyric acid from the culture system of 1).

Uses of Aspartase

The inventors have unexpectedly found that the aspartase of the present invention can be used for preparing a preparation for catalyzing the stereoisomeric catalytic reaction as below:

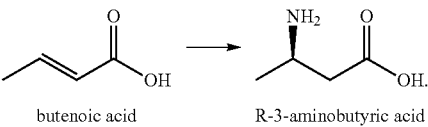

Equation I butenoic acid     R-3-aminobutyric acid

R-3-Aminobutyric Acid Producing Strain

The inventor also provides an engineered strain expressing the aspartase of the present invention, and the engineered strain (or the aspartase of the present invention, or an immobilized enzyme expressed thereof) is capable of converting butenoic acid to R-3-aminobutyric acid with high efficiency and high stereoselectivity. The conversion rate is ≥98% and the chiral ee value of R-3-aminobutyric acid is ≥99.9%.

In another preferred embodiment, the production strain is a bacteria. Preferably, the producing strain is *E. coli*. More preferably, the producing strain is *E. coli* BL21 (DE3).

The Main Advantages of the Invention are:

The invention can convert butenoic acid to R-3-aminobutyric acid with high efficiency and high stereoselectivity. After only 24 hours of reaction, the conversion rate is as high as ≥98% and the ee value is ≥99.9%, which greatly improves conversion efficiency, shortens reaction time, and reduces production cost.

The method of the invention has high conversion rate, low cost, high yield, short production cycle, simple process. The method is easy to enlarge and suitable for large scale production. The obtained R-3-aminobutyric acid has an extremely high ee value. It has great application prospects in the production of R-3-aminobutyric acid and downstream products using R-3-aminobutyric acid as a precursor.

The present invention will be further illustrated below with reference to the specific examples. It is to be understood that these examples are for illustrative purposes only and are not intended to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Percentages and parts are by weight unless otherwise stated.

The reagents and raw materials used in the invention are all commercially available. Unless defined otherwise, all technical and scientific terms used herein have the same meaning as commonly understood by the ordinary skilled in the art to which the invention belongs. Although any methods and materials similar or equivalent to those described herein can be used in the practice or testing of the present invention, the methods and materials described herein are preferred.

EXAMPLES

Example 1. Catalytic Synthesis of R-3-Aminobutyric Acid with AspA Wild-Type and the Detection Thereof 1.1 Preparation of AspA Wild Type Enzyme Solution Based on the amino acid sequence of AspA wild-type (SEQ ID NO: 5), a DNA sequence (SEQ ID NO: 6) encoding the AspA wild-type enzyme was synthesized and linked to pET28a by enzymes, wherein the restriction enzyme cutting sites were NdeI and HindIII. The linked vector was transformed into the host *E. coli* BL21 competent cells. The strain was inoculated in the TB medium, and cultured in a shaker at 37° C., 200 rpm until the OD600 value reached 4.0. Then IPTG having a concentration of 0.1 mM was added for induction, the temperature was adjusted to 28° C. and the culture was continued for 12 hours. The bacterial cells were collected by centrifugation at 4° C., and resuspended with phosphate buffer (50 mM, pH 7.0). The cells were homogenized and disrupted to obtain AspA wild-type enzyme solution.

Amino acid sequence of AspA wild type:

(SEQ ID NO: 5)
CLKQIIGSLKKKVHMSNNIRIEEDLLGTREVPADAYYGVHTLRAIENFYI
SNNKISDIPEFVRGMVMVKKAAAMANKELQTIPKSVANAIIAACDEVLNN
GKCMDQFPVDVYQGGAGTSVNMNTNEVLANIGLELMGHQKGEYQYLNPND
HVNKCQSTNDAYPTGFRIAVYSSLIKLVDAINQLREGFERKAVEFQDILK
MGR<u>T</u>QLQDAVPMTLGQEFRAFSILLKEEVKNIQRTAELLLEVNLGATAIG
TGLNTPKEYSPLAVKKLAEVTGFPCVPAEDLIEATSDCGAYVMVHGALKR
LAVKMSKICNDLRLLSSGPRAGLNEINLPELQAGSS<u>IMP</u>A<u>K</u>V<u>N</u>VVPEVVN
QVCFKVIGNDTTVTMAAEAGQLQLNVMEPVIGQAMFESVHILTNACYNLL
EKCINGITANKEVCEGYVYNSIGIVTYLNPFIGHHNGDIVGKICAETGKS
VREVVLERGLLTEAELDDIFSVQNLMHPAYKAKRYTDESEQ

Nucleic acid coding sequence of AspA wild type:

(SEQ ID NO: 6)
TGCCTGAAACAGATCATCGGTTCTCTGAAAAAAAAAGTTCACATGTCTAA
CAACATCCGTATCGAAGAAGACCTGCTGGGTACCCGTGAAGTTCCGGCTG
ACGCTTACTACGGTGTTCACACCCTGCGTGCTATCGAAAACTTCTACATC
TCTAACAACAAAATCTCTGACATCCCGGAATTCGTTCGTGGTATGGTTAT
GGTTAAAAAAGCTGCTGCTATGGCTAACAAAGAACTGCAGACCATCCCGA
AATCTGTTGCTAACGCTATCATCGCTGCTTGCGACGAAGTTCTGAACAAC
GGTAAATGCATGGACCAGTTCCCGGTTGACGTTTACCAGGGTGGTGCTGG
TACCTCTGTTAACATGAACACCAACGAAGTTCTGGCTAACATCGGTCTGG
AACTGATGGGTCACCAGAAAGGTGAATACCAGTACCTGAACCCGAACGAC
CACGTTAACAAATGCCAGTCTACCAACGACGCTTACCCGACCGGTTTCCG
TATCGCTGTTTACTCTTCTCTGATCAAACTGGTTGACGCTATCAACCAGC
TGCGTGAAGGTTTCGAACGTAAAGCTGTTGAATTCCAGGACATCCTGAAA
ATGGGTCGTACCCAGCTGCAGGACGCTGTTCCGATGACCCTGGGTCAGGA
ATTCCGTGCTTTCTCTATCCTGCTGAAAGAAGAAGTTAAAAACATCCAGC
GTACCGCTGAACTGCTGCTGGAAGTTAACCTGGGTGCTACCGCTATCGGT
ACCGGTCTGAACACCCCGAAAGAATACTCTCCGCTGGCTGTTAAAAAACT
GGCTGAAGTTACCGGTTTCCCGTGCGTTCCGGCTGAAGACCTGATCGAAG
CTACCTCTGACTGCGGTGCTTACGTTATGGTTCACGGTGCTCTGAAACGT
CTGGCTGTTAAAATGTCTAAAATCTGCAACGACCTGCGTCTGCTGTCTTC
TGGTCCGCGTGCTGGTCTGAACGAAATCAACCTGCCGGAACTGCAGGCTG
GTTCTTCTATCATGCCGGCTAAAGTTAACCCGGTTGTTCCGGAAGTTGTT
AACCAGGTTTGCTTCAAAGTTATCGGTAACGACACCACCGTTACCATGGC
TGCTGAAGCTGGTCAGCTGCAGCTGAACGTTATGGAACCGGTTATCGGTC
AGGCTATGTTCGAATCTGTTCACATCCTGACCAACGCTTGCTACAACCTG
CTGGAAAAATGCATCAACGGTATCACCGCTAACAAAGAAGTTTGCGAAGG

```
TTACGTTTACAACTCTATCGGTATCGTTACCTACCTGAACCCGTTCATCG

GTCACCACAACGGTGACATCGTTGGTAAAATCTGCGCTGAAACCGGTAAA

TCTGTTCGTGAAGTTGTTCTGGAACGTGGTCTGCTGACCGAAGCTGAACT

GGACGACATCTTCTCTGTTCAGAACCTGATGCACCCGGCTTACAAAGCTA

AACGTTACACCGACGAATCTGAACAG
```

1.2 Catalytic Synthesis of R-3-Aminobutyric Acid with AspA Wild-Type

The synthesis reacts in a 100 ml reaction system at 37° C. 100 mM HEPES buffer of pH 8.0 was added. 2 mM $MgCl_2$, 300 mM butenoic acid, 300 mM $NH_4Cl$ and 20 ml AspA wild-type enzyme solution were added, wherein the above concentrations were final concentrations.

The progress of the reaction was detected by HPLC. The reaction was completed at 24 h, and the conversion rate was <5%.

Calculation of conversion rate: the conversion rate is also referred to material conversion rate, which is numerically equal to the ratio of the butenoic acid consumed in the fermentation process to the total amount of butenoic acid at the beginning of the fermentation. It is usually expressed as a percentage and can be a molar ratio (mol %), can also be a weight ratio (wt %).

Example 2. Catalytic Synthesis of R-3-Aminobutyric Acid with AspA Mutant 1 and the Detection Thereof

2.1 Preparation of AspA Mutant 1 Enzyme Solution

All of the amino acids at the 4 mutation sites of AspA mutant 1 were mutated (see Tables 1 and 2). Based on the amino acid sequence of AspA mutant 1 (SEQ ID NO: 3), a DNA sequence (SEQ ID NO: 4) encoding the AspA mutant 1 enzyme was synthesized and linked to pET28a by enzymes, wherein the restriction enzyme cutting sites were NdeI and HindIII. The linked vector was transformed into the host *E. coli* BL21 competent cells. The strain was inoculated in the TB medium, and cultured in a shaker at 37° C., 200 rpm until the OD600 value reached 4.0. Then IPTG having a concentration of 0.1 mM was added for induction, the temperature was adjusted to 28° C. and the culture was continued for 12 hours. The bacterial cells were collected by centrifugation at 4° C., and resuspended with phosphate buffer (50 mM, pH 7.0). The cells were homogenized and disrupted to obtain AspA mutant 1 enzyme solution.

Amino Acid Sequence of AspA Mutant 1:

```
                                      (SEQ ID NO: 3)
CLKQIIGSLKKKVHMSNNIRIEEDLLGTREVPADAYYGVHTLRAIENFYI

SNNKISDIPEFVRGMVMVKKAAAMANKELQTIPKSVANAIIAACDEVLNN

GKCMDQFPVDVYQGGAGTSVNMNTNEVLANIGLELMGHQKGEYQYLNPND

HVNKCQSTNDAYPTGFRIAVYSSLIKLVDAINQLREGFERKAVEFQDILK

MGRCQLQDAVPMTLGQEFRAFSILLKEEVKNIQRTAELLLEVNLGATAIG

TGLNTPKEYSPLAVKKLAEVTGFPCVPAEDLIEATSDCGAYVMVHGALKR

LAVKMSKICNDLRLLSSGPRAGLNEINLPELQAGSSIIPAMVCPVVPEVV

NQVCFKVIGNDTTVTMAAEAGQLQLNVMEPVIGQAMFESVHILTNACYNL
```

LEKCINGITANKEVCEGYVYNSIGIVTYLNPFIGHHNGDIVGKICAETGK

SVREVVLERGLLTEAELDDIFSVQNLMHPAYKAKRYTDESEQ

Nucleic Acid Coding Sequence of AspA Mutant 1:

```
                                      (SEQ ID NO: 4)
TGCCTGAAACAAATCATTGGTAGCCTGAAGAAAAAAGTGCACATGAGCAA

TAACATTCGCATCGAAGAGGATCTGCTGGGTACACGTGAAGTGCCGGCAG

ATGCCTACTACGGTGTGCATACACTGCGCGCCATCGAAAATTTTTACATC

AGCAATAATAAAATCAGCGATATCCCGGAATTCGTGCGCGGCATGGTTAT

GGTGAAAAAAGCCGCCGCAATGGCCAACAAGGAACTGCAGACCATTCCGA

AGAGTGTGGCAAACGCCATTATCGCCGCCTGTGATGAAGTGCTGAACAAT

GGTAAATGCATGGATCAGTTTCCGGTGGACGTGTATCAAGGCGGCGCCGG

TACCAGCGTGAACATGAACACCAATGAGGTGCTGGCCAACATTGGTCTGG

AGCTGATGGGTCACCAGAAAGGCGAATACCAGTACCTGAACCCGAACGAT

CACGTGAACAAGTGTCAGAGCACAAATGACGCATACCCGACAGGCTTTCG

TATTGCCGTGTACAGTAGCCTGATCAAGCTGGTGGATGCCATCAATCAGC

TGCGTGAAGGCTTCGAGCGTAAGGCCGTTGAATTTCAGGACATCCTGAAA

ATGGGTCGTTGTCAGCTGCAGGATGCAGTGCCGATGACCCTGGGTCAGGA

ATTTCGCGCATTCAGCATCCTGTTAAAAGAGGAAGTGAAAAACATCCAGC

GTACCGCCGAACTGCTGCTGGAAGTTAACCTGGGTGCCACCGCCATCGGC

ACAGGCCTGAATACCCCGAAAGAGTATAGCCCGCTGGCCGTTAAAAAACT

GGCAGAGGTGACCGGTTTCCCGTGTGTGCCGGCAGAGGATCTGATCGAAG

CAACCAGCGATTGCGGTGCTTATGTTATGGTGCATGGTGCCCTGAAACGC

CTGGCCGTTAAGATGAGTAAAATCTGTAATGACCTGCGTCTGCTGAGCAG

CGGTCCTCGTGCAGGCCTGAACGAGATCAACCTGCCGGAACTGCAGGCCG

GCAGTAGCATCATCCCGGCCATGGTTTGCCCTGTGGTGCCGGAGGTGGTG

AATCAGGTGTGCTTCAAGGTGATCGGCAATGACACCACCGTGACAATGGC

CGCAGAGGCAGGCCAGCTGCAACTGAACGTGATGGAGCCGGTGATTGGCC

AGGCCATGTTTGAAAGCGTGCACATCTTAACCAACGCCTGCTACAACCTG

CTGGAGAAATGCATCAATGGTATTACCGCCAACAAAGAAGTTTGCGAGGG

TTACGTGTACAACAGCATTGGCATCGTGACCTATCTGAATCCGTTTATTG

GCCATCACAACGGCGACATTGTGGGCAAGATTTGCGCAGAGACCGGCAAA

AGTGTTCGCGAAGTGGTTCTGGAGCGCGGTTTACTGACCGAGGCCGAACT

GGATGACATTTTCAGCGTTCAAAATCTGATGCACCCGGCCTACAAAGCCA

AACGCTACACAGACGAAAGCGAGCAA
```

The measured enzyme activity was 5.1 U/ml. The enzyme activity U of the AspA mutant 1 enzyme is defined as: the amount of enzyme catalyzing the formation of 1 micromole of product R-3-aminobutyric acid from butenoic acid per minute is one enzyme unit, that is, 1 U.

Determination method is: 16 mL reaction solution (pH8.0) was added to a 100 ml Erlenmeyer flask, wherein the reaction solution contains 300 mmol/L butenoic acid, 4 mmol/L $MgCl_2$, 450 mmol/L ammonium chloride, 100 mmol/L HEPES buffer. The flask was sealed and the reaction solution and enzyme solution were placed in a 42° C. shaker respectively and incubated for 5-10 minutes. 4 ml of AspA mutant enzyme solution was added to the reaction solution, and immediately placed in a shaker at 42° C., 200 rpm to start the reaction. After 30 min, 1 ml of reaction solution was sampled, and 1 ml of acetonitrile was added to stop the reaction. The protein was removed by centrifugation. The supernatant was derivatized with 2, 4-dinitrofluorobenzene, and analyzed by HPLC (the enzyme activity was calculated based on the peak area).

2.2 Catalytic Synthesis of R-3-Aminobutyric Acid with AspA Mutant1

The synthesis reacts in a 100 ml reaction system at 37° C. 100 mM HEPES buffer of pH 8.0 was added. 2 mM $MgCl_2$, 300 mM butenoic acid, 300 mM $NH_4Cl$ and 20 ml AspA mutant 1 enzyme solution were added, wherein the above concentrations were final concentrations.

The progress of the reaction was detected by HPLC. The reaction was completed in 24 h, and the conversion rate was ≥98%, and the ee value was 99.9%.

Example 3. Catalytic Synthesis of R-3-Aminobutyric Acid with AspA Mutants 2-12 and the Detection Thereof 3.1 Preparation of AspA Mutants 2-12 Enzyme Solutions The specific mutations of AspA mutants 2-12 are shown in Tables 1 and 2. AspA mutants 2-5 are single amino acid mutation, AspA mutants 6-8 have amino acid mutations at two mutation sites, and AspA mutants 9-12 have amino acid mutations at three mutation sites.

Based on the amino acid sequences of AspA mutants 2-12, DNA sequences encoding the enzymes of each AspA mutant were synthesized respectively. The preparation method of the enzyme solution was the same as in Example 2.1.

TABLE 1

Positions and changes of mutant amino acids

| position | Wild type | Mutant |
|---|---|---|
| Mutation site 1 (amino acid at position 204) | Threonine (T) | Cysteine (C) |
| Mutation site 2 (amino acid at position 338) | Methionine (M) | Isoleucine (I) |
| Mutation site 3 (amino acid at position 341) | Lysine (K) | Methionine (M) |
| Mutation site 4 (amino acid at position 343) | Asparagine (N) | Cysteine (C) |

TABLE 2

Conversion rate of R-3-aminobutyric acid synthesis catalyzed by each mutant enzyme

| | Mutation site 1 | Mutation site 2 | Mutation site 3 | Mutation site 4 | Conversion rate |
|---|---|---|---|---|---|
| Wild type | − | − | − | − | * |
| Mutant 1 | + | + | + | + | **** |
| Mutant 2 | + | − | − | − | * |
| Mutant 3 | − | + | − | − | * |
| Mutant 4 | − | − | + | − | * |
| Mutant 5 | − | − | − | + | * |
| Mutant 6 | + | − | + | − | ** |
| Mutant 7 | − | + | + | − | ** |

TABLE 2-continued

Conversion rate of R-3-aminobutyric acid synthesis catalyzed by each mutant enzyme

| | Mutation site 1 | Mutation site 2 | Mutation site 3 | Mutation site 4 | Conversion rate |
|---|---|---|---|---|---|
| Mutant 8 | − | − | + | + | ** |
| Mutant 9 | + | + | − | + | ** |
| Mutant 10 | + | − | + | + | *** |
| Mutant 11 | − | + | + | + | *** |
| Mutant 12 | + | + | + | − | *** |

Note:
"+" represents mutation and "−" represents no mutation; "*" represents a conversion rate of <10%, "" represents a conversion rate of 10%-30%, "*" represents a conversion rate of 30%-70%, and "****" represents a conversion rate of >70%.

3.2 Catalytic Synthesis of R-3-Aminobutyric Acid with AspA Mutants 2-12

The experimental method was the same as in Example 2.2, and the AspA mutants 2-12 enzyme solutions were used to replace the AspA mutant 1 enzyme solution, respectively.

The results are shown in Table 2. The experimental results show that after 24 hours of reaction, AspA wild type (Example 1), mutant 1 (Example 2) and mutants 2-12 (Example 3) all have a certain stereoselectivity (selectively catalyzed to form R-3-aminobutyric acid), and the reaction time is significantly shortened. In addition, in terms of conversion rate and reaction speed, mutant 1 (four-site mutant) is significantly better than three-site mutants (such as mutants 9-12) and also better than two-site mutants (such as mutants 6-8), single site mutants (such as mutants 2-5) and wild type.

Comparative Example 1. Catalytic Synthesis of R-3-Aminobutyric Acid with AspB Mutant Derived from *Bacillus* and the Detection Thereof 1.1 Preparation of *Bacillus* AspB Mutant Enzyme Solution The AspB mutant enzyme solution was prepared by reference to the method in ChemCatChem, 2014, 6, 965-968. The amino acid sequence of the AspB mutant is shown in SEQ ID NO: 1, and the nucleic acid coding sequence is shown in SEQ ID NO: 2.

Amino Acid Sequence of AspB Mutant:

(SEQ ID NO: 1)
NTDVRIEKDFLGEKEIPKDAYYGVQTIRATENFPITGYRIHPELIKSLGI

VKKSAALANMEVGLLDKEVGQYIVKAADEVIEGKWNDQFIVDPIQGGAGT

SINMNANEVIANRALELMGEEKGNYSKISPNSHVNMSQSTNDAFPTATHI

AVLSLLNQLIETTKYMQQEFMKKADEFAGVIKMGRCHLQDAVPILLGQEF

EAYARVIARDIERIANTRNNLYDINMGATAVGTGLNADPEYISIVTEHLA

KFSGIIPLRSAQHLVDATQNTDCYTEVSSALKVCMINMSKIANDLRLMAS

GPRAGLSEIVLPARQPGSSIIPGMVCPVMPEVMNQVAFQVFGNDLTITSA

SEAGQFELNVMEPVLFFNLIQSISIMTNVFKSFTENCLKGIKANEERMKE

YVEKSIGIITAINPHVGYETAAKLAREAYLTGESIRELCIKYGVLTEEQL

NEILNPYEMIHPGIAGRK

Nucleic Acid Coding Sentience of AspB Mutant:

(SEQ ID NO: 2)
AACACCGATGTGCGCATTGAGAAGGACTTCCTGGGTGAAAAGGAAATCCC

GAAGGATGCCTATTACGGCGTGCAGACCATCCGTGCCACAGAGAACTTTC

CTATCACCGGCTACCGCATCCATCCGGAACTGATTAAGAGCCTGGGCATT

GTGAAGAAAAGCGCCGCACTGGCAAACATGGAGGTGGGTCTGCTGGATAA

GGAAGTGGGTCAGTACATCGTGAAGGCCGCCGACGAAGTTATTGAAGGTA

AGTGGAACGATCAGTTTATCGTGGACCCGATTCAGGGCGGCGCAGGTACA

AGCATTAATATGAACGCCAACGAAGTGATCGCAAACCGCGCCCTGGAACT

GATGGGTGAGGAAAAGGGCAACTATAGCAAGATCAGCCCGAACAGCCACG

TTAACATGAGCCAGAGCACCAATGATGCATTTCCGACCGCAACCCATATT

GCCGTGCTGAGTCTGCTGAATCAGCTGATCGAGACCACCAAGTACATGCA

GCAGGAGTTTATGAAGAAGGCCGACGAATTCGCCGGCGTTATTAAAATGG

GCCGCTGCCATCTGCAAGACGCCGTTCCGATTCTGCTGGGTCAGGAGTTT

GAGGCTTATGCTCGTGTGATCGCACGTGACATTGAGCGCATCGCCAATAC

CCGTAACAACCTGTATGATATCAACATGGGCGCAACCGCCGTTGGCACAG

GCCTGAATGCAGACCCGGAGTACATTAGCATCGTTACCGAGCACCTGGCC

AAATTTAGCGGTCATCCGCTGCGTAGTGCCCAGCATCTGGTTGATGCCAC

CCAGAATACAGATTGCTACACCGAGGTGAGCAGTGCCCTGAAAGTGTGCA

TGATCAATATGAGTAAGATTGCCAACGACCTGCGCTTAATGGCAAGTGGC

CCGCGCGCAGGCCTGAGCGAAATTGTTCTGCCTGCACGCCAACCGGGCAG

CAGCATCATCCCTGGTATGGTGTGTCCGGTGATGCCGGAAGTGATGAACC

AGGTTGCCTTCCAGGTGTTCGGTAACGACCTGACCATCACAAGCGCAAGC

GAAGCAGGCCAGTTCGAGTTAAACGTGATGGAACCTGTGCTGTTTTTTAA

CTTAATTCAGAGCATCAGTATTATGACAAATGTTTTTAAGTCTTTTACCG

AAAACTGTCTGAAAGGTATCAAGGCCAACGAGGAACGCATGAAAGAGTAT

GTGGAAAAAGCATTGGCATCATCACCGCCATCAACCCGCATGTGGGCTA

TGAGACAGCCGCCAAACTGGCCCGCGAAGCCTATTTAACCGGCGAGAGTA

TTCGCGAGCTGTGTATCAAGTACGGCGTGCTGACCGAAGAGCAGCTGAAC

GAGATCCTGAATCCGTACGAGATGATCCATCCTGGCATTGCAGGTCGCAA
A

The measured enzyme activity was 3.8 U/ml. The enzyme activity U of the AspB mutant enzyme is defined as: the amount of enzyme catalyzing the formation of 1 micromole of product R-3-aminobutyric acid from butenoic acid per minute is one enzyme unit, that is, 1 U.

Determination method is: 16 mL reaction solution (pH8.5) was added to a 100 ml Erlenmeyer flask, wherein the reaction solution contains 300 mmol/L butenoic acid, 4 mmol/L $MgCl_2$, 450 mmol/L ammonium chloride, 100 mmol/L HEPES buffer. The flask was sealed and the reaction solution and enzyme solution were placed in a 42° C. shaker respectively and incubated for 5-10 minutes. 4 ml of enzyme solution was added to the reaction solution, and immediately placed in a shaker at 42° C., 200 rpm to start the reaction. After 30 min, 1 ml of reaction solution was sampled, and 1 ml of acetonitrile was added to stop the reaction. The protein was removed by centrifugation. The supernatant was derivatized with 2, 4-dinitrofluorobenzene, and analyzed by HPLC (the enzyme activity was calculated based on the peak area).

1.2 Catalytic Synthesis of R-3-Aminobutyric Acid with AspB Mutant

The synthesis reacts in a 100 ml reaction system at 37° C. 100 mM HEPES buffer of pH 8.0 was added. 2 mM $MgCl_2$, 300 mM butenoic acid, 300 mM $NH_4Cl$ and 20 ml AspB mutant enzyme solution were added, wherein the above concentrations were final concentrations.

The progress of the reaction was detected by HPLC. The reaction was performed for 24 hours, the conversion rate was 42% and the ee value was 99.9%. The reaction was performed for 100 hours, the conversion rate was 60%, and the ee value was 99.7%.

The results show that, compared with the method in the comparative example, the method of the present invention utilizes an aspartase derived from *E. coli* that has stereoisomeric catalytic activity to efficiently and highly stereoselectively convert butenoic acid to R-3-aminobutyric acid. The method greatly improves conversion efficiency, shortens reaction time, and reduces production costs. The method features a high yield, a high conversion rate, low costs, a short production cycle, a simple process, ease of enlargement, suitability for mass production and the like. The present invention has been completed on the basis of this.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. An R-3-aminobutyric acid production strain expressing a polypeptide, wherein the polypeptide is an exogenous aspartase derived from *E. coli* and is used to catalyze a stereoisomeric catalytic reaction as shown below:

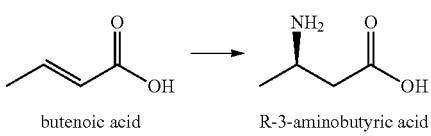

butenoic acid      R-3-aminobutyric acid wherein the exogenous aspartase is a mutant having 90% sequence identity to the amino acid sequence of SEQ ID NO: 5, possessing two to four amino acid mutations in the amino acid sequence corresponding to the wild type aspartase shown in SEQ ID NO: 5; or wherein the exogenous aspartase is a mutant having an amino acid mutation selected from the group consisting of threonine (T) at position 204, methionine (M) at position 338, Lysine (K) at position 341, asparagine (N) at position 343, and a combination thereof.

2. The R-3-aminobutyric acid production strain of claim 1, wherein the mutant has one or more mutations selected from the group consisting of T204C, M338I, K341M, N343C, and a combination thereof.

3. The R-3-aminobutyric acid production strain of claim 1, wherein the exogenous aspartase has the amino acid sequence shown in SEQ ID NO: 3.

4. A polynucleotide encoding a polypeptide, wherein the polypeptide is an exogenous aspartase obtained from *E. coli* and is used to catalyze a stereoisomeric catalytic reaction as shown below:

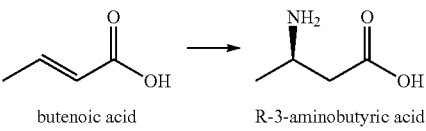

butenoic acid      R-3-aminobutyric acid wherein the exogenous aspartase is a mutant having 90% sequence identity to the amino acid sequence of SEQ ID NO: 5, which has two to four amino acid mutations in the amino acid sequence corresponding to the wild type aspartase shown in SEQ ID NO: 5; or wherein the exogenous aspartase is a mutant having an amino acid mutation selected from the group consisting of threonine (T) at position 204, methionine (M) at position 338, Lysine (K) at position 341, asparagine (N) at position 343, and a combination thereof.

5. The polynucleotide of claim 4, wherein the exogenous aspartase has the amino acid sequence shown in SEQ ID NO: 3.

6. The polynucleotide of claim 4, wherein the polynucleotide has a sequence as shown in SEQ ID NO: 4.

7. The polynucleotide of claim 4, wherein the polynucleotide has over 95% homologous to the sequence of SEQ ID NO: 4, and encodes a polypeptide as shown in SEQ ID NO: 3.

* * * * *